United States Patent
Morrison et al.

(10) Patent No.: US 9,452,954 B2
(45) Date of Patent: Sep. 27, 2016

(54) METHOD FOR DECARBOXYLATION OF AMINO ACIDS VIA IMINE FORMATION

(71) Applicant: University of Georgia Research Foundation, Inc., Athens, GA (US)

(72) Inventors: Richard W. Morrison, Watkinsville, GA (US); Douglas Michael Jackson, Athens, GA (US)

(73) Assignee: University of Georgia Research Foundation, Inc.

( * ) Notice: Subject to any disclaimer, the term of this patent is extended or adjusted under 35 U.S.C. 154(b) by 34 days.

(21) Appl. No.: 14/210,655

(22) Filed: Mar. 14, 2014

(65) Prior Publication Data

US 2014/0275569 A1 Sep. 18, 2014

Related U.S. Application Data (60) Provisional application No. 61/783,052, filed on Mar. 14, 2013.

(51) Int. Cl.
| | |
|---|---|
| *C07D 209/14* | (2006.01) |
| *C07D 209/16* | (2006.01) |
| *C07D 233/64* | (2006.01) |
| *C07B 37/06* | (2006.01) |
| *C07C 249/02* | (2006.01) |
| *C07C 209/68* | (2006.01) |
| *C07C 213/08* | (2006.01) |

(52) U.S. Cl.
CPC ............. *C07B 37/06* (2013.01); *C07C 209/68* (2013.01); *C07C 213/08* (2013.01); *C07C 249/02* (2013.01); *C07D 209/14* (2013.01); *C07D 209/16* (2013.01); *C07D 233/64* (2013.01); *C07C 2101/16* (2013.01)

(58) Field of Classification Search
CPC . C07D 209/14; C07D 209/16; C07D 233/64
See application file for complete search history.

(56) References Cited

U.S. PATENT DOCUMENTS

| | | |
|---|---|---|
| 6,403,806 B1 | 6/2002 | Yeh et al. |
| 2008/0214864 A1 | 9/2008 | Omeis et al. |

FOREIGN PATENT DOCUMENTS

| | | |
|---|---|---|
| EP | 1586553 B1 | 4/2009 |

OTHER PUBLICATIONS

Galat, A.; Friedman, H.L . . . A New Method for the Isolation of Histamine. J. Am. Chem. Soc. 1949. 71, 3976.
Hashimoto, M.; Eda, Y.; Osani, Y.; Iwai, T.; Aoki, S . . . A Novel Decarboxylation of α-Amino Acids. A Facile Method of Decarboxylation by the Use of 2-Cyclohexen-1-One as a Catalyst. Chem. Lett. 1986, 6, 893.
Martins, C.P.B., et al. Fingerprint analysis of thermolytic decarboxylation of tryptophan to tryptamine catalyzed by natural oilsJ. Chromatogr. A. 2008, 1210, 115.

*Primary Examiner* — Rebecca Anderson
(74) *Attorney, Agent, or Firm* — Thomas | Horstemeyer, LLP (57) ABSTRACT

The present application provides methods for decarboxylation of amino acids via imine formation with a catalyst under pressurized and superheated conditions in either a microwave or oil bath.

24 Claims, 4 Drawing Sheets

Scheme 1

FIG. 4

Scheme 2 a. Microwave Procedure b. Oil Bath Procedure

FIG. 5

METHOD FOR DECARBOXYLATION OF AMINO ACIDS VIA IMINE FORMATION

CROSS-REFERENCE TO RELATED APPLICATION

This application claims priority to and the benefit of U.S. provisional patent application entitled "Method for Decarboxylation of Amino Acids Via Imine Formation", Ser. No. 61/783,052 filed Mar. 14, 2013 and incorporated herein by reference in its entirety.

BACKGROUND

Decarboxylation of amino acids is an important synthetic route to biologically active amines. Current procedures for synthesis of biologically relevant amines suffer from extremely long reaction times and difficulty with solvent and byproduct removal. Thus, an alternative method of isolation for the free amines that is faster than previously reported methods and allows for high yields and solvent removal is needed to prevent thermal degradation, particularly for high boiling point product amines.

SUMMARY

Briefly described, the present disclosure provides methods of decarboxylation of amino acids via imine formation at elevated temperatures.

In embodiments, the methods of decarboxylation of amino acids according to the present disclosure include combining, in a pressurized reaction vessel, a mixture of an amino acid, a solvent, and a catalyst and heating the mixture at about 180° C., or more, for about 5 minutes, or more, such that the amino acid is converted to its imine. In embodiments, the solvent has a lower boiling point than cyclohexanol and does not produce a maximum vapor pressure exceeding the vessel limit. The methods of the present disclosure, in embodiments, can be carried out with microwave heating or heating in an oil bath.

Methods for decarboxylation of amino acids, according to some embodiments of the present disclosure, include combining, in a pressurized reaction vessel, a mixture of an amino acid, n-propanol as solvent, and from about 0.1 to about 2 mol equivalents of R-carvone as catalyst and heating the mixture in a microwave to a temperature of about 180° C. to about 195° C. for at least 5 minutes. In embodiments, the methods further include optionally heating the mixture in the microwave to a temperature of about 180° C. to about 195° C. for up to an additional 25 min, cooling the reaction vessel to a temperature below the boiling point of n-propanol, adding an acid to the reaction mixture in the vessel, and re-heating the acid reaction mixture in the microwave to a temperature of about 180° C. to about 195° C. to hydrolyze the imine to form an amine and to convert unreacted carvone to carvacrol.

In embodiments, the methods of amino acid decarboxylation of present disclosure include combining, in a pressurized reaction vessel, a mixture of an amino acid, n-propanol as solvent, and from about 0.1 to about 2 mol equivalents of R-carvone as catalyst and heating the mixture in an oil bath at a temperature of about 180° C. to about 195° C. for about 5 minutes. In embodiments, the methods further include optionally heating the mixture in the oil bath at a temperature of about 180° C. to about 195° C. for up to an additional 25 min, cooling the reaction vessel to a temperature below the boiling point of n-propanol, adding an acid to the reaction mixture in the vessel, and re-heating the acid reaction mixture in the oil bath at a temperature of about 180° C. to about 195° C. to hydrolyze the imine to form an amine and to convert unreacted carvone to carvacrol.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Many aspects of the disclosed methods can be better understood with reference to the drawings, which are discussed in the description and examples below. The components in the drawings are not necessarily to scale, emphasis instead being placed upon clearly illustrating the relevant principles of the present disclosure.

DESCRIPTION

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range.

Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. Terms defined in references that are incorporated by reference do not alter definitions of terms defined in the present disclosure or should such terms be used to define terms in the present disclosure they should only be used in a manner that is inconsistent with the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic and inorganic chemistry, material science, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for methods of decarboxylation of amino acids (including both naturally occurring amino acids and synthetic analogs) to amines. The methods of the present disclosure provide for a quick, simple and effective decarboxylation of amino acids via imine formation with a catalyst under superheated conditions.

Enzymatic decarboxylation of amino acids occurs in many organisms and provides a synthetic option for the decarboxylation of the amino acid L-histidine[1]. Many amino acids have also been shown to undergo decarboxylation upon reflux in a high boiling solvent, such as cyclohexanol, in the presence of a ketone, such as cyclohex-2-ene-1-one[2] or acetophenone[3]. This is believed to occur through an active conformation of an imine intermediate. However, for synthesis of some of the more biologically relevant amines, previously reported procedures are slow and are complicated by difficult purification procedures to remove byproducts and high boiling solvents.

More recently, two processes for the removal of product free amines by distillation from a high boiling solvent have been reported[5]. These methods may assist with the problem of solvent removal for lower boiling product amines, but reaction times were still extremely long and the success of these procedures for difficult decarboxylations, such as L-histidine to histamine, are unsubstantiated and have not been reproduced. Thus, an alternative method of isolation is needed to prevent thermal degradation, especially for free amines with high boiling point.

Embodiments of the methods for decarboxylation of amino acids of the present disclosure include combining an amino acid, a solvent, and a catalyst in a pressurized reaction vessel to form a mixture. The mixture is then heated at a temperature of at least about 180° C. (e.g., about 180° C., or more) for at least 5 minutes, or more. During heating, the reaction takes place to convert the amino acid to its imine. The resulting reaction mixture in the vessel includes the imine, the solvent, any unreacted catalyst, and any unreacted amino acid. If the reaction is not complete (in embodiments, a complete reaction is indicated by the reaction mixture turning from a slurry into a clear liquid), additional heating is performed, as described below.

Various solvents can be used in the methods of the present disclosure, but an advantage of the present methods is that a solvent with greater volatility and lower boiling point provides advantages over the traditional cyclohexanol used in previous, time consuming methods. Thus, various solvents with a lower boiling point than traditional solvents for conversion of amino acids to amines can be used. In embodiments, the solvent does not produce a maximum vapor pressure exceeding the vessel limit. Thus, the solvent system can be tailored to the parameters of the reaction vessel and vice versa. In embodiments, the reaction vessel is a 15 bar reaction vessel. In embodiments, the solvent is a short chain alcohol or water. Solvents that can be used in the methods of the present disclosure include, but are not limited to, water, n-butanol, n-pentanol, isopropanol, ethanol, methanol, n-propanol, and combinations of these solvents. In embodiments of the methods of the present disclosure, the solvent is n-propanol.

Various catalysts can also be used in the methods of the present disclosure. Some examples of catalysts that can be used in the methods of the present disclosure include keytone or aldehyde catalysts, including but not limited to, ceyclohex-2-ene-1-one, acetophenone, R-carvone, S-carvone, and acetone. In embodiments, the catalyst is an alpha or beta unsaturated keytone. In embodiments of the present disclosure, the catalyst is R-carvone.

As described in the examples below, the load of the catalyst is a factor affecting the reaction rate and ease of purification. It was found that 0.1 mole equivalents of catalyst produced an appreciable catalytic effect and that the effect appeared to peak at about 2 mole equivalents. Thus, in embodiments, the mixture includes from about 0.1 to about 2 mole equivalents of catalyst.

In the methods of the present disclosure, the heating can be performed in a microwave or traditional oil bath. In some embodiments using the oil bath for heating, the oil can be, but is not limited to, silicone oil. In embodiments, the mixture is heated in a microwave to a temperature of about 180° C. to about 190° C. for about 5 min to about 10 min. In embodiments, a microwave reactor with a thermometer and automatic feedback loop is used to maintain the temperature. After the initial heating, if the reaction mixture is not complete (e.g., not clear, or other criteria, as applicable) a second heating step can be conducted. In embodiments, the mixture is re-heated in the microwave to about 190° C. for about 5 to about 25 min longer.

When an oil bath is used, additional heating time may be needed, since it is more difficult to maintain a constant heat in the oil bath. In embodiments, the mixture is heated in an oil bath at a temperature of about 180° C. to about 190° C. for about 5 min to about 20 min. In embodiments, if the reaction is not complete after the first heating, an additional heating can be conducted, such as by heating again at about 180° C. to about 190° C. for about 5 to about 20 min longer. To account for changes in temperature of the oil bath when the room temperature reaction vessel is added, the oil bath may be heated to a higher temperature prior to addition of the reaction vessel. For instance, in embodiments, the oil bath is heated to a temperature of about 210° C. prior to addition of the reaction vessel and brought back to a temperature between about 185° C. to about 190° C. after addition of the reaction vessel. This effect is mitigated by increasingly large bath volume.

After the heating steps, the amino acid will be substantially converted to its imine. To achieve high yield of amine from the imine, a hydrolysis step can be added. Hydrolysis can be achieved by heating in acid. Acids, such as, but not limited to HCl, can be used in the methods of the present disclosure. In embodiments, the methods include cooling the reaction vessel to a temperature below the boiling point of the solvent, adding an acid to the reaction mixture in the vessel, and heating the acid reaction mixture to about 50° C., or more, to hydrolyze the imine to form an amine.

In embodiments, the catalyst can be recovered from the reaction mixture by conducting the acid heating step at a temperature of about 80° C., with gentle reflux to hydrolyze the imine in equilibrium. When the catalyst is carvone, and the gentle reflux is conducted at about 80° C., the carvone is not isomerized to carvacrol, and the carvone can be recovered via extraction with diethyl ether. In embodiments, after extraction of carvone, any remaining unreacted carvone can be isomerized to carvacrol by heating at a temperature of about 180° C., or more, for about 5 min, or more.

However, greater purity of amine product is possible if the acid heating step is conducted at higher temperatures, such as above about 180° C., to isomerize the carvone to carvacrol during the hydrolysis of the imine with acid. Thus, in embodiments, the acid reaction mixture is heated to about 180° C., or more, for about 5 min., or more, to hydrolyze the imine to form an amine and to isomerize any unreacted catalyst. In embodiments, the acid reaction mixture is heated at about 185° C. to about 190° C. for about 5 min, or more. In embodiments, the acid is HCl. In embodiments the acid is 2M HCl. In some embodiments, such as when the products and/or amino acids are sensitive to acid during hydrolysis at 180° C., hydrolysis at 80° C. with soxhlet extraction, for removal of catalyst, can be performed instead.

After hydrolysis of the imine in acid, the unreacted catalyst and solvent can be removed by washing with water and organic solvent (e.g. an ethyl solvent, such as, but not limited to, diethyl ether). The corresponding amine acid or amine salt (e.g. amine hydrochloride or dihydrochloride salt) can be recovered by distilling off the solvent and water. The washing and distillation step can be repeated as necessary. In embodiments the reaction mixture is washed three times with ether and water solvent. In embodiments, after washing and distilling off the water and solvent, the amine salt can be dried (e.g., in an oven).

The above methods of the present disclosure can be conducted with any amino acid where it is desirable to convert the amino acid to the corresponding amine. Some exemplary amino acid that can be used in the methods of the present disclosure include, but are not limited to, histidine, isoleucine, lysine, phenylalanine, tryptophan, tyrosine, glycine, alanine, valine, proline, leucine, and threonine. Amino acids suitable for decarboxylation according to the methods of the present disclosure also include synthetic amino acids and other non-naturally occurring amino acid analogs. In accordance with standard nomenclature, amino acid residues are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). As used herein the term "amino acid" refers to either natural and/or unnatural or synthetic amino acids, including glycine and both the D or L optical isomers, and amino acid analogs and peptidomimetics.

As described in the examples below, in embodiments of the present disclosure methods of rapid decarboxylation of L-histidine and other L-amino acids have been accomplished via stable imine formation with R-carvone, and other catalysts, with subsequent one-pot hydrolysis under solvent superheated conditions using both conventional heating and microwave radiation. Although described in greater detail in the example below, briefly described, in an embodiment, the amino acid and R-carvone in a solvent of n-propanol are sealed in a suitable 15 bar microwave vessel with magnetic stirring. Decarboxylation is rapid (5-20 min) as the vessels are heated to about 190° C. over 5 min. The formed R-carvone imines are stable at room temperature in aqueous acid.

In embodiments, an additional 5 min period of heating is performed in one-pot fashion. At a temperature exceeding about 180° C., R-carvone is isomerized to carvacrol which drives the reaction to completion. In some embodiments, approximately 80% of the R-carvone can be recovered via extraction with diethyl ether if the hydrolysis is conducted at about 80° C. In some embodiments, greater amounts of catalyst can be recovered if the 80° C. hydrolysis is conducted in a soxhlet extractor with an organic solvent of boiling point 80° C. or greater such as, but not limited to, toluene. In some embodiments, the products and/or amino acids proved sensitive to acid during hydrolysis at 180° C. In these cases the 80° C. hydrolysis with soxhlet extraction provided a solution. In other embodiments, to obtain high product purity, residual R-carvone is isomerized to carvacrol, for easy removal. In embodiments, the carvacrol is then extracted away with diethyl ether, and water is removed via evaporation under reduced pressure. The entire conversion from amino acid to amine hydrochloride or dihydrochloride salt as appropriate was accomplished in less than 2 hours in all cases, followed by oven drying with isolated yields of 60-90%.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

Now having described the embodiments of the disclosure, in general, the following examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLE

The following examples describe decarboxylation of L-histidine and other L-amino acids via imine formation with R-carvone and other catalysts with subsequent one-pot hydrolysis under solvent superheated conditions using both conventional heating and microwave radiation. Decarboxylation was more rapid (5-20 min) than previous methods as the vessels were heated to 190° C. over 5 min. Approximately 80% of the R-carvone could be recovered via extraction with diethyl ether when the hydrolysis was conducted at 80° C. To obtain a higher purity product, a high temperature hydrolysis was conducted to isomerize residual R-carvone to carvacrol. Isolated yields of amine hydrochloride salts were comparable or improved over previous methods ranging from 60-90%. Given the exceptionally clean 1H NMR spectra and simplicity of the procedure, purity of hydrochloride salts was estimated to be >99% by 1H NMR.

Materials and Methods 5 mmol scale microwave experiments were performed in Milestone 25 mL 15 bar glass pressure reactors inside the Milestone Start SYNTH microwave oven with external infrared temperature control. Traditional heating experiments were performed in silicone oil in the same reaction vessels. Solvents and reagents were purchased from Sigma-Aldrich and used without additional purification. FT NMR experiments were recorded at 400 MHz in a solvent of $D_2O$.

General "One-Pot" Procedure for the Decarboxylation of Amino Acids

A magnetic stir bar, 3 mL of n-PrOH, 10 mmol of R-Carvone, and 5 mmol of amino acid were charged to a pressure vessel. The vessel was heated from room temperature to 190° C. over 5 min with stirring. If necessary the reaction vessel was maintained at 190° C. for additional time until the slurry became clear. The vessel was allowed to cool to below the solvent boiling point, carefully vented to release evolved $CO_2$, and 10 mL of 2M HCl was added. The vessel was heated to 190° C. over 5 min with stirring and allowed to cool. The aqueous reaction mixture was washed three times with 25 mL of ether and water solvent distilled off from the hydrochloride salt. The hydrochloride salt was transferred to a vacuum oven and dried overnight at 150° C. and 10 Torr. The hydrochloride salt was then weighed and analyzed via IR and NMR.

methylamine hydrochloride, $\delta_H$ 2.44 s; $\delta_C$ 24.5 ethylamine hydrochloride, $\delta_H$ 1.10 3H t J=8, 2.88 2H q J=8; $\delta_C$ 11.7, 35.1

2-methylpropan-1-amine hydrochloride, $\delta_H$ 0.83 6H d J=4, 1.79 1H m J=8, 2.69 2H d J=8; $\delta_C$ 18.8, 26.2, 46.3 pyrrolidine hydrochloride, $\delta_H$ 1.83 4H t J=4, 3.11 4H t J=4; $\delta_C$ 23.6, 45.4

3-methylbutan-1-amine hydrochloride, $\delta_H$ 0.75 6H d J=4, 1.38 2H q J=8, 1.48 1H m J=8, 2.85 2H t J=8; $\delta_C$ 21.28, 24.87, 35.43, 37.87

1-aminopropan-2-ol hydrochloride, $\delta_H$ 1.08 3H d J=4, 2.73 1H dd J=8, 2.95 1H dd J=12, 3.88 1H m J=4; $\delta_C$ 19.54, 45.46, 63.83 histamine dihydrochloride, $\delta_H$ 3.00 2H t J=8, 3.18 2H t J=8, 7.23 1H s, 8.50 1H s; $\delta_C$ 22.26, 38.11, 117.08, 128.49, 134.00 tryptamine hydrochloride, $\delta_H$ 2.97 2H t J=9, 3.13 2H t J=8, 7.01 1H t J=4, 7.07-7.12 2H m, 7.34 1H d J=4, 7.49 1H d J=4; $\delta_C$ 22.88, 40.03, 109.36, 112.30, 118.54, 119.68, 122.44, 124.53, 126.70, 136.69

2-methyl-1-butylamine hydrochloride $\delta_H$ 0.71 3Ht J=8, 0.78 3Hd J=8, 1.02 1H septet J=8, 1.22 1H septet J=8, 1.55 1Ho J=8, 2.59-2.64 1Hm, 2.76-2.80 1H m; $\delta_C$ 10.07, 15.75, 25.94, 32.48, 44.75 cadaverine dihydrochloride $\delta_H$ 1.28 2H p J=8, 1.54 4H p J=8, 2.84 4H t J=8; $\delta_C$ 22.75, 26.32, 39.33 tyramine hydrochloride $\delta_H$ 2.75 2H t J=8, 3.06 2H t J=8, 6.73 2H d J=8, 7.04 2H d J=8; $\delta_C$ 31.95, 40.83, 115.90, 128.55, 130.32, 154.65

2-phenylethylamine hydrochloride $\delta_H$ 2.82 2H t J=8, 3.10 2H t J=8, 7.12-7.26 5H m; $\delta_C$ 32.73, 40.55, 127.30, 128.88, 163.03, 170.53

Results and Discussion

Addressing the problem of long reaction times required for the decarboxylation of many amino acids such as histidine (>40 hrs) using extant procedures, it was envisioned that chemistry at temperatures above the reflux temperature of cyclohexanol (~160° C.) may provide a solution. However, in earlier efforts a significant amount of effort had been devoted to the removal of cyclohexanol and other high boiling solvents at the expense of yield and efficiency. An advantage to using a nonpolar alcohol, such as cylcohexanol, as solvent was the solubility of the amine product and insolubility of amino acids, thus allowing for visual determination of reaction completion (from slurry to clear solution). Rather than employ a higher boiling solvent system, which would yield the same difficulties as seen in the conventional methods, the possibility of a pressurized reaction system using a solvent with a lower normal boiling point was investigated in the present example.

Both microwave promoted and hot oil bath systems were investigated, using a sealed 15 bar maximum pressure reaction vessel. While many solvents satisfy the criterion of greater volatility, the search was limited to a series of short chain alcohol solvents in order to promote microwave absorption. Decarboxylation in aprotic solvents (microwave transparent) was observed to be slower when performed in an oil bath. Among the short chain alcohol solvents and water, n-butanol, n-pentanol, and isopropanol proved to absorb microwaves insufficiently, while ethanol, methanol, and water dissolve the reactant amino acid at the optimum reaction temperatures of >185° C., potentially hindering determination of reaction completion. Ethanol and methanol also require vessels that can withstand higher vapor pressure to achieve the optimum reaction temperature. An optimum solvent for visual inspection of reaction completion that could also reach the desired temperature without exceeding the maximum vapor pressure and could be removed easily after reaction completion was found to be n-propanol. This solvent achieves a maximum temperature of 190° C. (calibrated +/−2° C.) in a 1200 W instrument with a vapor pressure of 15 bar according to the Clausius-Ciaperyon equation. It should be noted that other (even nonpolar) solvents should also prove effective when heating in an oil bath so long as the maximum vapor pressure does not exceed the vessel's rated limit. However, reactions performed neat resulted in poor yield and aprotic solvents failed to promote decarboxylation even in the oil bath.

Figure 3:
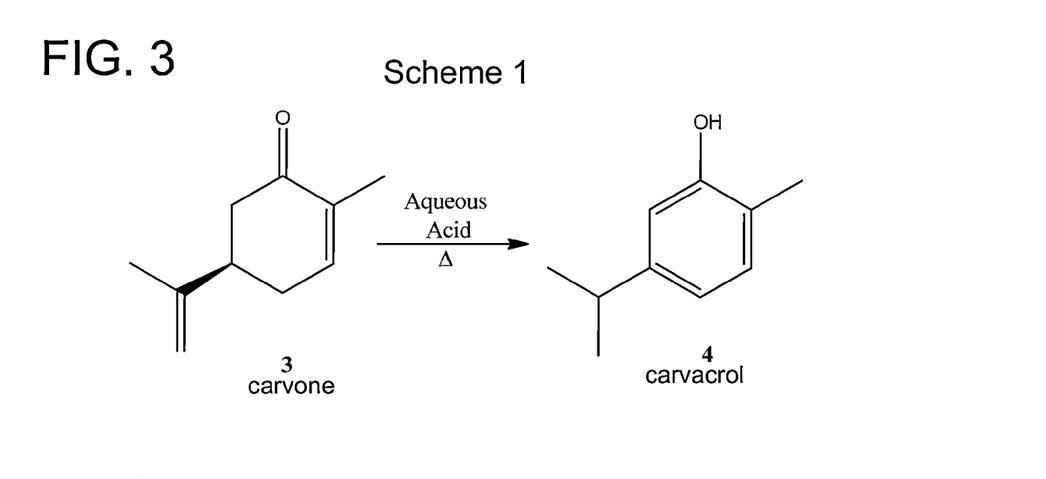
FIG. 3 illustrates the isomerization of carvone to carvacrol in aqueous acid, which facilitates its removal from the reaction product by basic extraction.

Another factor affecting the reaction rate and overall ease of purification of the product mixture was the identity and load of the catalyst. In conventional methods, a 1% v/v of cyclohex-2-ene-1-one (2) has been reported for histidine decarboxylation[2]; however, others[3] have reported difficulty in repeating these results without a substantially higher catalyst load. Significant impurities were also observed in the resulting reaction mixture by those authors, and in later attempts to reproduce the experiments. These authors alternatively used acetophenone (1) to modest success[3] for the decarboxylation of histamine at 20 mol % in >40 hr. It was postulated that the greater the stability of the imine, the greater the reaction rate at a given catalyst load, and, indeed, cyclohex-2-ene-1-one (2) proved to provide a greater catalytic effect at 20 mol % than acetophenone (1). On a belief that the enone functionality of cyclohex-2-ene-1-one provides some advantage over the benzyl ketone and given its toxicity and expense of, an alternative was selected for testing in the present examples. R-carvone (3), the natural product of spearmint oil, was selected for its potential to retain the catalytic advantage over acetophenone while providing an alternative method of removal of the catalyst based on the isomerization reaction of R-carvone (3) to carvacrol (4) (Scheme 1, FIG. 3).

Figure 1:
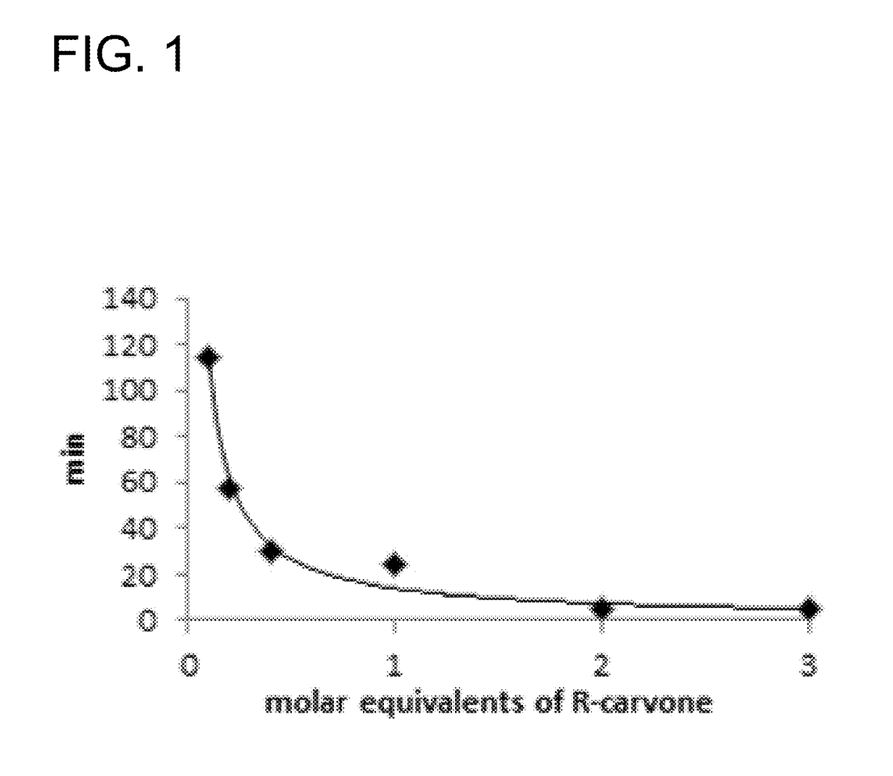
FIG. 1 is a graph illustrating the reaction time in minutes for a series of microwave assisted decarboxylations of phenylalanine in n-propanol at 190° C. with various levels of R-carvone as catalyst.

It was also observed during these experiments that the rate of reaction significantly increased at the higher catalyst load, an effect maximizing at about 2 mole equivalents for both cyclo-hex-2-ene-1-one (2) and R-carvone (3). The reaction times in minutes of a series of microwave assisted decarboxylations of phenylalanine in n-propanol at 190° C., varying the load of R-carvone (3) catalyst, are given in FIG. 1. Table 1, below, compares several catalysts at the 2 equivalent load for performance on a series of decarboxylations.

Figure 2A:
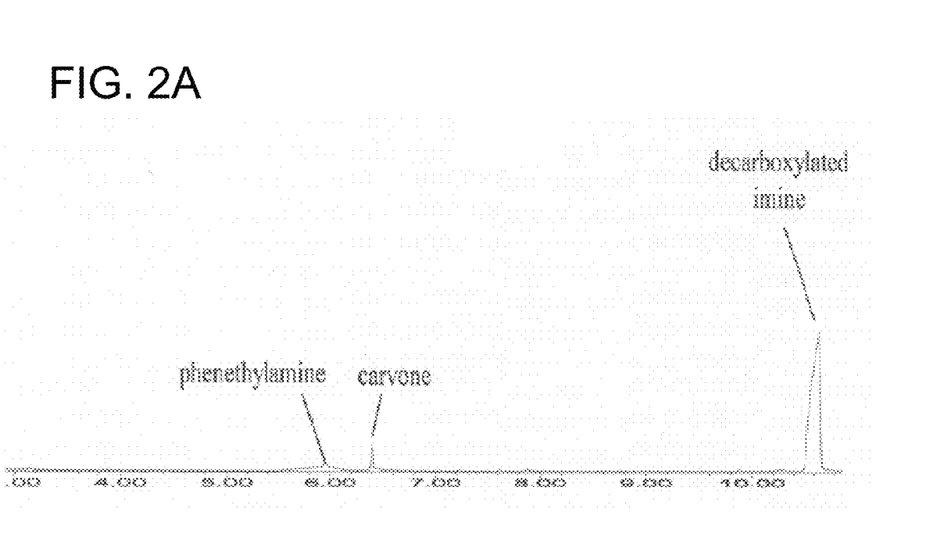
FIG. 2A is a GC-MS spectrum of the reaction product of the decarboxylation of phenylalanine with carvone.
Figure 2B:
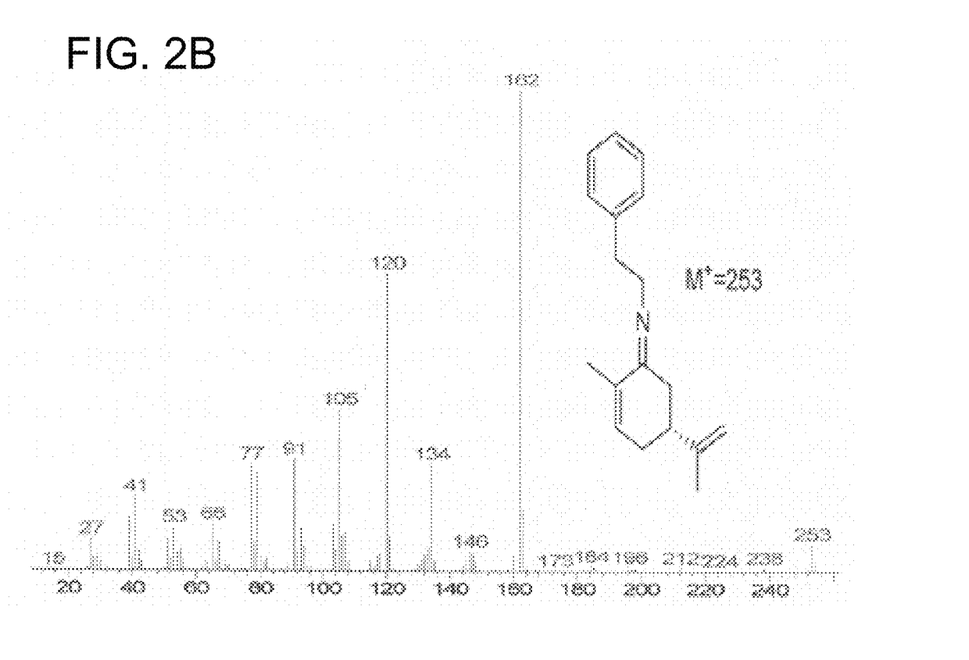
FIG. 2B is a gas chromatograph of the crude product of decarboxylation of phenylalanine in the presence of 2.0 mole equivalents of R-carvone after workup in aqueous acid. The EI mass spectrum of the imine of phenethylamine and carvone is clearly shown as the predominant species.

Considering that the reaction is thought to occur through a carboxylic acid imine intermediate and given the observed rise in impurities as a result of increasing the catalyst load from the Hashimoto procedure, the fate of the decarboxylated imine was then investigated as follows. A large excess of carvone was added to the reaction mixture to attempt to capture all product amine as an imine with carvone. The imine was then transferred into an aqueous acid mixture, excess carvone removed via ether wash, and then returned to an organic phase via neutralization with NaOH solution. A significant degree of hydrolysis was expected; however, in these observations, the imine of the decarboxylated product was quite stable and persisted as demonstrated by the GC-MS spectrum and gas chromatograph (FIGS. 2A and 2B) of the product mixture of decarboxylated phenylalanine.

It was observed that only after heating in acid at >50° C. did the hydrolysis occur. Even after one pot reflux with many times the reaction volume of 2.0 M HCl, it proved difficult to adequately remove all traces of the imine at system equilibrium. Each conventional method of amino acid decarboxylation fails to account for the quantity of imine that may remain, thus lowering the yield and purity of the crude product and leading to further purification.

It was envisioned that the complete hydrolysis of the imine could be accomplished via the removal of the catalyst in situ. If a low boiling ketone, such as acetone, or other aldehyde catalyst were used, it would be sealed in the pressurized vessel during decarboxylation and then distilled away from the product mixture during imine hydrolysis. Several decarboxylations were accomplished using acetone as catalyst; however, the vapor pressure of pure acetone at the optimal temperature exceeded the recommended safe operating pressure of the reaction vessel so an alternative option was desired. Thus, R-carvone (3), an inexpensive, readily available alpha unsaturated ketone natural product, was selected. The isomerization reaction of carvone produces carvacrol (FIG. 3), a phenolic natural product that would be inert to the product amine.

Using R-carvone as catalyst, a 5 min reflux at 190° C. in 2 M HCl hydrolyzed the imine and isomerized carvone to carvacrol. The carvacrol was then easily removed via ether extraction. It should be noted that gentle reflux at 80° C. allows the imine to hydrolyze in equilibrium, and ~80% of the carvone catalyst may be recovered via three sequential refluxes and extractions. If the carvone is recovered in this way, a final high temperature reflux can be performed to isomerize residual carvone to carvacrol for isolation of amine hydrochloride salt of highest purity. The overall synthetic process is highlighted in Scheme 2, illustrated in FIG. 4.

Figure 4:
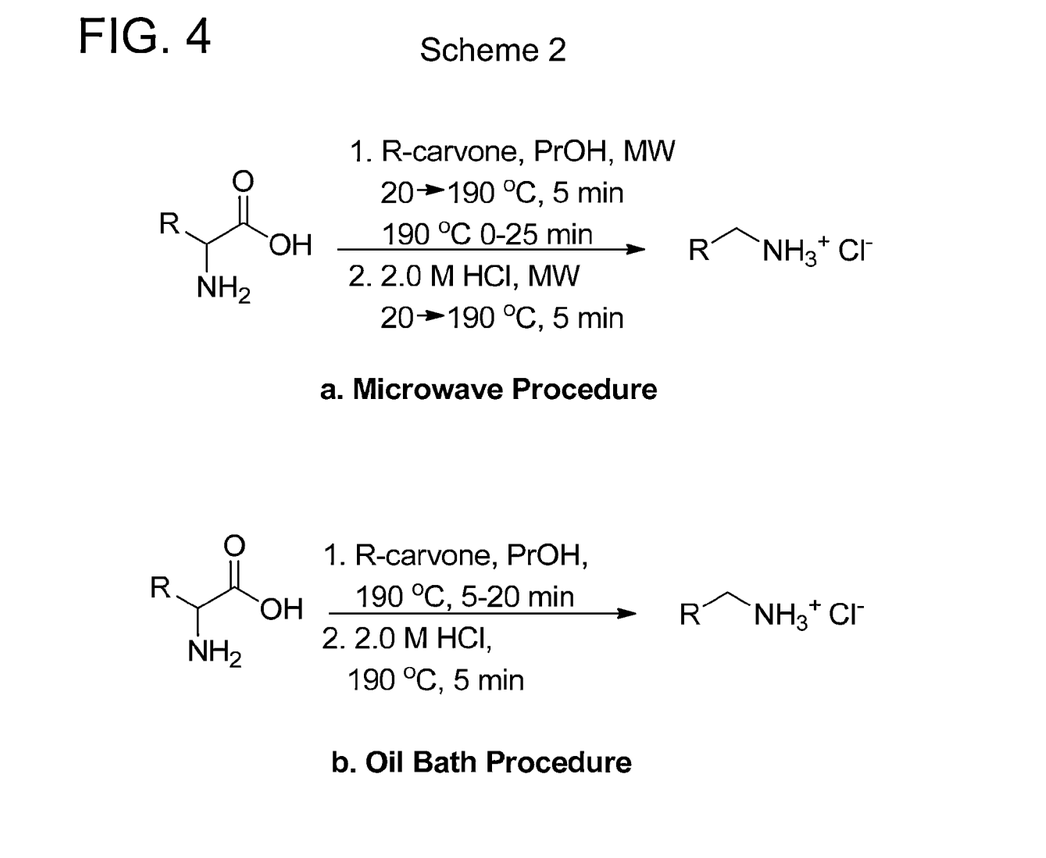
FIG. 4 illustrates a reaction scheme (scheme 1) for a one-pot decarboxylation procedure.

The reaction times for the decarboxylation of selected amino acids of interest is reported in Table 2, below, for both microwave and oil bath heating. Isolated yields of the amine hydrochloride or dihydrochloride salts are also given in Table 2 for the optimized reaction conditions highlighted in reaction Scheme 2 (FIG. 4). The slight differences in the overall reaction times reported between MW heating and oil bath heating are the result of the differences in the experimental procedure. In the microwave reactor, initial heating is rapid, occurring over a 5 min period, and temperature is computer controlled by an infrared thermometer in a continuous feedback system to +/−2° C. Conventional heating was performed in a preheated bath with observed temperature oscillations of about +/−5° C. For example, in some experiments the reaction vessels were added to a pre-heated oil bath system at ~210° C., which, upon addition of the room temperature vessels, dropped to ~185° C., where the temperature was maintained as close to 190° C. as possible (typically to within ±5° C.).

Figure 5:
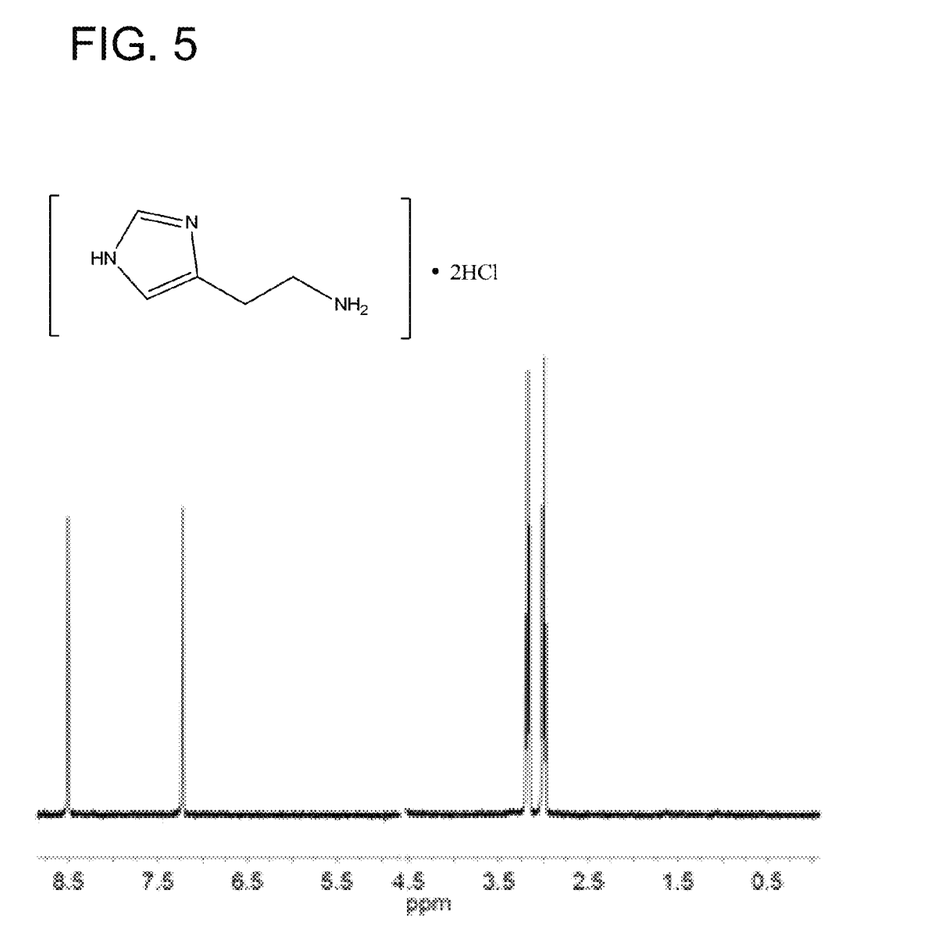
FIG. 5 illustrates an HNMR of histamine dihydrochloride with solvent $D_2O$ suppressed.

A representative HNMR is shown in FIG. 5 for the product amine salts in $D_2O$. The solvent peak arising from acidic proton exchange was suppressed. Note that no organic impurities were observed in H NMR of the hydrochloride salts using DMSO-$d_6$ as solvent.

TABLE 1

Reaction times in minutes at the 2.0 molar equivalent load for various catalysts for a series of decarboxylations under MW conditions at 190° C.

| Amino Acid | Acetophenone (1) | Cyclohex-2-ene-1-one (2) | R-carvone (3) | S-carvone | acetone |
|---|---|---|---|---|---|
| Phe | 5 | 5 | 5 | 7 | 5 |
| His | 25 | 25 | 25 | 50 | * |
| Trp | 5 | 5 | 5 | 5 | 7 |
| Tyr | 10 | 6 | 20 | 16 | 40 |

* completed in approximately 72 hours in an oil bath

TABLE 2

Decarboxylation reaction times and yields for a series of amino acids under optimized conditions heated by either MW irradiation or via oil bath.

| Conditions | Amino Acid | Reaction Time (min) | Yield (%) |
|---|---|---|---|
| MW* | His | 25 | 87 |
|  | Ile | 9 | 69 |
|  | Lys | 12 | 73 |
|  | Phe | 5 | 76 |
|  | Trp | 5 | 68 |
|  | Tyr | 20 | 53 |
|  | Gly | 13 | 86 |
|  | Ala | 5 | 60 |
|  | Val | 5 | 79 |
|  | Pro | 5 | 80 |
|  | Leu | 5 | 72 |
|  | Thr | 5 | 59** |
| Oil Bath | His | 12 | 92 |
|  | Ile | 12 | 76 |
|  | Lys | 17 | 93 |
|  | Phe | 5 | 78 |
|  | Trp | 9 | 72 |
|  | Tyr | 40 | 67 |
|  | Gly | 40 | 67 |
|  | Ala | 38 | 74 |
|  | Val | 9 | 55 |
|  | Pro | 5 | 48 |
|  | Leu | 5 | 69 |
|  | Thr | 12 | 41** |

*reaction times represent total programmed time
**80° C. hydrolysis with soxhlet extraction performed

REFERENCES

Each of the following references are incorporated herein by reference in their entirety.
1. Galat, A.; Friedman, H. L. *J. Am. Chem. Soc.* 1949. 71, 3976.
2. Hashimoto, M.; Eda, Y.; Osani, Y.; Iwai, T.; Aoki, S. *Chem. Lett.* 1986, 6, 893.
3. Yeh, W. L. et al.; 2002. U.S. Pat. No. 6,403,806 B1.
4. Martins, C. P. B., et al. *J. Chromatogr. A.* 2008, 1210, 115.
5. Omeis, M., et al. 2008. U.S. Pat. No. 7,485,756
6. Yaegashi, K., et al., 2009, EPO Patent: EP1586553

The invention claimed is:

1. A method for decarboxylation of amino acids, the method comprising:

combining, in a pressurized reaction vessel, a mixture of an amino acid, a solvent, and a catalyst, wherein the solvent has a lower boiling point than cyclohexanol and does not produce a maximum vapor pressure exceeding the vessel limit;

heating the mixture at about 180° C., or more, for about 5 minutes, or more, wherein the amino acid is converted to its imine;

cooling the reaction vessel to a temperature below the boiling point of the solvent;

adding an acid to the reaction mixture in the vessel; and heating the acid reaction mixture to about 50° C., or more, to hydrolyze the imine to form an amine.

2. The method of claim 1, wherein the solvent is a short chain alcohol or water.

3. The method of claim 1, wherein the solvent is selected from the group consisting of: water, n-butanol, n-pentanol, isopropanol, ethanol, methanol, and n-propanol.

4. The method of claim 1, wherein the solvent is n-propanol.

5. The method of claim 1, wherein the catalyst is selected from the group consisting of: ceyclohex-2-ene-1-one, acetophenone, R-carvone, S-carvone, and acetone.

6. The method of claim 1, wherein the catalyst is R-carvone.

7. The method of claim 1 when the amount of catalyst is from about 0.1 to about 2 mole equivalents.

8. The method of claim 1, wherein mixture is heated in a microwave to a temperature of about 180° C. to about 190° C. and maintained at a temperature of about 180° C. to about 190° C. for about 5 minutes to about 10 minutes.

9. The method of claim 8, wherein the mixture is heated in a microwave to a temperature of about 190° C. for about 5 minutes, and if the reaction mixture is not clear after the 5 minutes of heating, the mixture is heated in the microwave to about 190° C. for about 5 to about 25 minutes longer.

10. The method of claim 1, wherein the mixture is heated in an oil bath at a temperature of about 180° C. to about 190° C. for about 5 minutes to about 20 minutes.

11. The method of claim 10, wherein, the mixture is heated in an oil bath at a temperature of about 180° C. to about 190° C. for about 5 minutes, and wherein, if the reaction mixture is not clear after the 5 minutes of heating, the mixture is heated at about 180° C. to about 190° C. for an additional time of about 5 to about 20 minutes.

12. The method of claim 10, wherein the oil bath is heated to a temperature of about 210° C. prior to addition of the reaction vessel and brought back to a temperature between about 185° C. to about 190° C. after addition of the reaction vessel.

13. The method of claim 1, wherein the catalyst is carvone and the acid reaction mixture is heated to about 80° C., or more, with gentle reflux to hydrolyze the imine in equilibrium.

14. The method of claim 13, further comprising recovering the catalyst via extraction and performing an additional reflux at a temperature of about 180° C., or more, for about 5 minutes, or more, to isomerize any unreacted catalyst.

15. The method of claim 1, wherein the acid reaction mixture is heated to about 180° C., or more, for about 5 minutes, or more, to hydrolyze the imine to form an amine and to isomerize any unreacted catalyst.

16. The method of claim 1, wherein the acid reaction mixture is heated to about 185° C. to about 190° C. for about 5 minutes, or more, to hydrolyze the imine to form an amine and to isomerize any unreacted catalyst.

17. The method of claim 1, wherein the acid is HCl.

18. The method of claim 1, wherein the amino acid is selected from the group consisting of: histidine, isoleucine, lysine, phenylalanine, tryptophan, and tyrosine.

19. A method for decarboxylation of amino acids, the method comprising:
   combining, in a pressurized reaction vessel, a mixture of an amino acid, n-propanol as solvent, and from about 0.1 to about 2 mol equivalents of R-carvone or S-carvone as catalyst; and
   heating the mixture in a microwave to a temperature of about 180° C. to about 195° C. for about 5 minutes, or more, to convert the amino acid to an imine;
   optionally heating the mixture in the microwave to a temperature of about 180° C. to about 195° C. for up to an additional 25 minutes;
   cooling the reaction vessel to a temperature below the boiling point of n-propanol;
   adding an acid to the reaction mixture in the vessel; and
   re-heating the acid reaction mixture in the microwave to a temperature of about 180° C. to about 195° C. to hydrolyze the imine to form an amine and to convert unreacted carvone to carvacrol.

20. The method of claim 19, further comprising:
   removing unreacted solvent and carvacrol; and
   recovering the amine.

21. The method of claim 20, wherein removing unreacted solvent and carvacrol comprises washing the reaction mixture with ether and water solvent and distilling off the water, ether, solvent, and recovering an amine salt.

22. A method for decarboxylation of amino acids comprising:
   Combining, in a pressurized reaction vessel, a mixture of an amino acid, n-propanol as solvent, and from about 0.1 to about 2 mol equivalents of R-carvone or S-carvone as catalyst; and
   heating the mixture in an oil bath at a temperature of about 180° C. to about 195° C. for about 5 minutes to convert the amino acid to an imine;
   optionally heating the mixture in the oil bath at a temperature of about 180° C. to about 195° C. for up to an additional 25 minutes;
   cooling the reaction vessel to a temperature below the boiling point of n-propanol;
   adding an acid to the reaction mixture in the vessel;
   and re-heating the acid reaction mixture in the oil bath at a temperature of about 180° C. to about 195° C. to hydrolyze the imine to form an amine and to convert unreacted carvone to carvacrol.

23. The method of claim 1, wherein the catalyst is carvone and the solvent is selected from the group consisting of: water, n-butanol, n-pentanol, isopropanol, ethanol, methanol, and n-propanol.

24. A method for decarboxylation of amino acids, the method comprising:
   combining, in a pressurized reaction vessel, a mixture of an amino acid, a solvent, and a catalyst;
   heating the mixture at about 180° C., or more, at a pressure of greater than 1 atm for about 5 minutes, or more, wherein the amino acid is converted to its imine;
   cooling the reaction vessel to a temperature below the boiling point of the solvent;
   adding an acid to the reaction mixture in the vessel; and
   heating the acid reaction mixture to about 50° C., or more, to hydrolyze the imine to form an amine.

* * * * *